United States Patent
Drake et al.

(10) Patent No.: US 6,489,528 B2
(45) Date of Patent: Dec. 3, 2002

(54) AROMATICS PRODUCTION FROM OXYGENATED HYDROCARBONS

(75) Inventors: Charles A. Drake, Nowata, OK (US); An-hsiang Wu, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 10/042,544

(22) Filed: Jan. 10, 2002

(65) Prior Publication Data

US 2002/0099249 A1 Jul. 25, 2002

Related U.S. Application Data

(62) Division of application No. 09/361,885, filed on Jul. 27, 1999, now Pat. No. 6,372,680.

(51) Int. Cl.[7] .............................. C07C 1/20; C07C 1/207
(52) U.S. Cl. ..................... 585/469; 585/408; 585/409
(58) Field of Search ................................ 585/469, 408, 585/409

(56) References Cited

U.S. PATENT DOCUMENTS

| | | | |
|---|---|---|---|
| 4,049,573 A | 9/1977 | Kaeding | 252/432 |
| 4,429,174 A | 1/1984 | Teng et al. | 585/426 |
| 4,499,317 A | 2/1985 | Liu et al. | 585/438 |

OTHER PUBLICATIONS

U.S. patent application Ser. No. 08/854,646, filed May 12, 1997.
U.S. patent application Ser. No. 09/078,030, filed May 13, 1998.
U.S. patent application Ser. No. 09/144,940, filed Sep. 1, 1998.
U.S. patent application Ser. No. 09/154,301, filed Sep. 16, 1998.
U.S. patent application Ser. No. 09/262,799, filed Mar. 4, 1999.

Primary Examiner—Thuan D. Dang
(74) Attorney, Agent, or Firm—Michael E. Lee

(57) ABSTRACT

A catalyst system comprising a first solid material comprising a silicoaluminophosphate and a second solid material comprising a zeolite and a compound containing zinc and a metal selected from the group consisting of Group IIIA and Group VIB, and a method of preparing such catalyst system, are disclosed. The thus-obtained catalyst system is employed as a catalyst in the conversion of at least a portion of a hydrocarbon feedstock comprising oxygenated hydrocarbons to aromatics (BTX), and, in particular, xylenes. In an alternate embodiment, a hydrocarbon feedstock comprising oxygenated hydrocarbons are converted to aromatics by sequentially contacting the hydrocarbon feedstock with the first solid material and then the second solid material.

15 Claims, No Drawings

AROMATICS PRODUCTION FROM OXYGENATED HYDROCARBONS

This is a Division of application Ser. No. 09/361,885, filed Jul. 27, 1999, now U.S. Pat. No. 6,372,680.

BACKGROUND OF THE INVENTION

The present invention relates to the field of hydrocarbon upgrading processes. In another aspect, the invention relates to the conversion of oxygenated hydrocarbons to aromatics.

Developments in zeolite catalysts useful in hydrocarbon conversion processes have led to the use of zeolite catalysts for the conversion of oxygenated hydrocarbons to aromatics. The term "oxygenated hydrocarbons" as employed herein is defined to include hydrocarbons containing aliphatic moieties such as, but not limited to, alcohols, halides, mercaptans, sulfides, amines, ethers, and carbonyl compounds (aldehydes, ketones, carboxylic acids and the like) or mixtures thereof.

It is known to convert oxygenated hydrocarbons to olefins and aromatics in the presence of catalysts which contain a zeolite, as is described in U.S. Pat. No. 4,049,573. However, there are ever present incentives, including the selectivity to specific aromatics such as xylene, for the development of new, more effective and/or more practical catalyst systems and methods of preparing them.

SUMMARY OF THE INVENTION

It is an object of this invention to provide a novel hybrid catalyst system effective for converting at least a portion of a hydrocarbon feedstock comprising at least one oxygenated hydrocarbon to a reaction product comprising at least one aromatic.

It is yet another object of this invention to provide a method for making a novel hybrid catalyst system effective for converting at least a portion of a hydrocarbon feedstock comprising at least one oxygenated hydrocarbon to a reaction product comprising at least one aromatic.

Yet another object of this invention is to provide an improved process for the conversion of at least a portion of a hydrocarbon feedstock comprising at least one oxygenated hydrocarbon to a reaction product comprising at least one aromatic.

It is yet another object of this invention to provide a novel hybrid catalyst system which when used in the conversion of oxygenated hydrocarbons results in preferential production of aromatics.

A further object of this invention is to provide a novel hybrid catalyst system which when used in the conversion of oxygenated hydrocarbons results in preferential production of xylenes.

According to a first embodiment of the present invention, a catalyst system which can be used in the conversion of oxygenated hydrocarbons to aromatics is provided. The novel catalyst system comprises a first solid material comprising a silicoaluminophosphate and a second solid material comprising a zeolite, a zinc component and a metal selected from the group consisting of Group IIIA and Group VIB of the CAS version of the Periodic Table of the Elements, Hawley's Condensed Chemical Dictionary, 11th edition and combinations of any two or more thereof.

According to a second embodiment of the present invention, a method is provided for preparing a catalyst system, which can be used in the conversion of oxygenated hydrocarbons to aromatics, comprising blending the first solid material and the second solid material from the first embodiment.

According to a third embodiment of the present invention, a method is provided for preparing a catalyst system, which can be used in the conversion of oxygenated hydrocarbons to aromatics, comprising placing the first solid material from the first embodiment into a contacting vessel and placing the second solid material from the first embodiment into the contacting vessel such that a hydrocarbon feedstock comprising at least one oxygenated hydrocarbon charged to the contacting vessel contacts the first solid material prior to contacting the second solid material.

According to a fourth embodiment of the present invention, a method is provided for preparing a catalyst system, which can be used in the conversion of oxygenated hydrocarbons to aromatics, comprising placing the first solid material from the first embodiment into a first contacting vessel, placing the second solid material from the first embodiment into a second contacting vessel, and operating the catalyst system such that a hydrocarbon feedstock comprising at least one oxygenated hydrocarbon charged to the catalyst system contacts the first solid material prior to contacting the second solid material.

According to a fifth embodiment of the present invention, a process is provided for the conversion of at least a portion of a hydrocarbon feedstock comprising at least one oxygenated hydrocarbon to aromatics by contacting under conversion conditions the hydrocarbon feedstock with the novel catalyst system of the first embodiment prepared by the method of the second, third or fourth embodiment.

Other objects and advantages of the invention will become apparent from the detailed description and the appended claims.

DETAILED DESCRIPTION OF THE INVENTION

According to the first embodiment of the present invention the inventive catalyst system can comprise, consist essentially of, or consist of a first solid material comprising a catalytically effective amount of a silicoaluminophosphate (SAPO) and a second solid material comprising a catalytically effective amount of a zeolite, a catalytically effective amount of a zinc component and a catalytically effective amount of a metal selected from the group consisting of Group IIIA and Group VIB, and combinations of any two or more thereof.

The SAPO material used in preparing the first solid material can be any SAPO that, when used in conjunction with a zeolite material, is effective in the conversion of oxygenated hydrocarbons to aromatics.

SAPO materials exhibit properties of both aluminosilicate zeolites and aluminophosphates. The SAPO's have a three-dimensional microporous crystal framework structure comprising $PO_2$, $AlO_2$ and $SiO_2$ tetrahedral units. The chemical composition (anhydrous) is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular SAPO species involved, and "x", "y" and "z" represent the mole fractions of silicon, aluminum and phosphorus, respectively.

Examples of such templating agents include, but are not limited to, tetramethylammonium hydroxide, tetraethylammonium hydroxide, and tetrapropylammonium hydroxide. Further details relating to the formation of SAPO compositions, including molar amounts of each oxide source, can be found in the Lok et al. U.S. Pat. No. 4,440,871, the entire disclosure of which is expressly incorporated herein by reference.

SAPO compositions useful in the present invention include, but are not limited to, SAPO-4, SAPO-5, SAPO-11, SAPO-16, SAPO-17, SAPO-20, SAPO-31, SAPO-34, SAPO-35, SAPO-37, SAPO-40, SAPO-41, SAPO-42, and SAPO-44, described in Lok et al. referenced above. The presently more preferred SAPO is SAPO-34.

The SAPO can be combined or mixed with a binder material in a liquid such as water or a hydrocarbon, by any means known to one skilled in the art such as stirring, blending or kneading following which the resulting mixture can be extruded into pellets or tablets by any method known to those skilled in the art. The mixture can then be dried in air at a temperature in the range of from about 20° C. to about 125° C., for a time period in the range of from about 0.5 hour to about 4 hours under any pressures that accommodate the temperatures, preferably atmospheric pressure.

Any binders known to one skilled in the art for use with a SAPO are suitable for use herein. Examples of suitable binders include, but are not limited to, aluminas such as for example α-alumina and γ-alumina; silicas; alumina-silica; aluminum phosphate; aluminum chlorohydrate; clays such as kaolinite, halloysite, vermiculite, chlorite, attapulgite, smectite, montmorillonite, illite, saconite, sepiolite, palygorskite, and combinations of any two or more thereof. Because these binders are well known to one skilled in the art, descriptions of which are omitted herein. The presently preferred binder, if employed, is silica.

The SAPO, whether bound in a SAPO-binder mixture, and whether or not extruded, can be calcined by any suitable means or method known in the art whereby it is exposed to an atmosphere of inert gas, air or combinations thereof, under temperature and pressure conditions and for a period of time that suitably provide a calcined SAPO.

The calcination temperature is generally in the range of from about 200° C. to about 1000° C., preferably from about 300° C. to about 750° C., and most preferably from 350° C. to 650° C., the calcination pressure is generally in the range of from about 0 to about 50 atmospheres (atm), preferably from about 0.1 to about 30 atm, and most preferably from 0.5 to 10 atm. The calcination can be performed in either an air atmosphere or an inert atmosphere or a combination thereof for a time period in the range of from about 0.1 hour to about 30 hours, preferably from about 2 hours to about 20 hours, and most preferably from 3 hours to 15 hours.

The zeolite material used in preparing the second solid material can be any zeolite that, when used in conjunction with a SAPO material, is effective in the conversion of oxygenated hydrocarbons to aromatics.

Preferably, the zeolite has a constraint index (as defined in U.S. Pat. No. 4,097,367, the disclosure of which is incorporated herein by reference) in the range of from about 0.4 to about 12, preferably from about 2 to about 9. Generally, the molar ratio of $SiO_2$ to $Al_2O_3$ in the crystalline framework of the zeolite is at least about 5:1 and can range up to infinity. Preferably, the molar ratio of $SiO_2$ to $Al_2O_3$ in the zeolite framework is in the range of from about 8:1 to about 200:1, more preferably in the range of from about 12:1 to about 100:1. Preferred zeolites include, but are not limited to, ZSM-5, ZSM-8, ZSM-11, ZSM-12, ZSM-35, ZSM-38, and mixtures of any two or more thereof. Some of these zeolites are also known as "MFI" or "Pentasil" zeolites. The presently more preferred zeolite is ZSM-5.

The zeolite can be acid leached by any suitable means or method to give an acid-leached zeolite. For such acid leaching, it is preferred for the zeolite to be soaked with an acid solution by any suitable means known in the art for contacting the zeolite with such acid solution. The acid solution used to treat the zeolite can be a solution of any acid that suitably provides for the leaching of aluminum atoms from the zeolite particles. Preferably, the acid concentration in this solution is about 1–10 equivalents per liter. Examples of such suitable acids include sulfuric, phosphoric, nitric and hydrochloric. The preferred acid solution is aqueous hydrochloric acid. The zeolite is soaked in the acid solution (preferably at a temperature of about 50–100° C.) for a period upwardly to about 15 hours, but, preferably from 0.1 hour to 12 hours. After soaking, the resultant acid-leached zeolite is washed free of the acid and then can be dried or calcined, or both.

The calcination temperature is generally in the range of from about 200° C. to about 1000° C., preferably from about 300° C. to about 750° C., and most preferably from 350° C. to 650° C., the calcination pressure is generally in the range of from about 0 to about 50 atmospheres (atm), preferably from about 0.1 to about 30 atm, and most preferably from 0.5 to 10 atm. The calcination can be performed in either an air atmosphere or an inert atmosphere or a combination thereof for a time period in the range of from about 0.1 hour to about 30 hours, preferably from about 2 hours to about 20 hours, and most preferably from 3 hours to 15 hours.

The second solid material comprises a catalytically effective amount of a zeolite which may or may not have been acid-leached, a catalytically effective amount of a zinc component, a catalytically effective amount of a metal selected from the group consisting of Group IIIA and Group VIB and, optionally, a binder material. The preferred metal is boron.

The zeolite can, optionally, be combined or mixed with a binder material in a liquid such as water or a hydrocarbon, by any means known to one skilled in the art such as stirring, blending or kneading following which the resulting mixture can be extruded into pellets or tablets by any method known to those skilled in the art. The mixture can then be dried in air at a temperature in the range of from about 20° C. to about 125° C., for a time period in the range of from about 0.5 hour to about 4 hours under any pressures that accommodate the temperatures, preferably atmospheric pressure.

Any binders known to one skilled in the art for use with a zeolite are suitable for use herein. Examples of suitable binders include, but are not limited to, aluminas such as for example α-alumina and γ-alumina; silicas; alumina-silica; aluminum phosphate; aluminum chlorohydrate; clays such as kaolinite, halloysite, vermiculite, chlorite, attapulgite, smectite, montmorillonite, illite, saconite, sepiolite, palygorskite, and combinations of any two or more thereof. Because these binders are well known to one skilled in the art, descriptions of which are omitted herein. The presently preferred binder, if employed, is silica.

The zinc component and metal can be incorporated into the zeolite or zeolite-binder mixture by any suitable means or method known in the art for incorporating metallic elements into a substrate material. A preferred method is the use of any standard incipient wetness technique for impregnating the zeolite with the zinc component and metal thereby forming an impregnated zeolite. The preferred method uses a liquid impregnation solution containing the desirable concentrations of zinc and the metal selected from the group consisting of Group IIIA and Group VIB so as to ultimately provide the second solid material having the required concentrations of zinc and the metal selected from the group consisting of Group IIIA and Group VIB. The incorporation of the zinc component and metal can be performed as one step along with the optional combination of the zeolite and the binder.

It is particularly desirable to use for the impregnation of the zeolite, which may or may not have been acid-leached, an aqueous solution containing the zinc component and the metal. The preferred impregnation solution is an aqueous solution formed by dissolving a compound comprising zinc and a metal selected from the group consisting of Group IIIA and Group VIB in water. It is preferable to use somewhat of an acidic solution to aid in the dissolution of the compound. The acid used to acidify the impregnation solution is preferably nitric acid.

Examples of suitable compounds comprising zinc and a metal selected from the group consisting of Group IIIA and Group VIB for incorporating into the zeolite include, but are not limited to, zinc hexaborate, zinc molybdate, zinc chromate, zinc tungstate and zinc aluminate.

The amounts of zinc and the metal selected from the group consisting of Group IIIA and Group VIB incorporated or impregnated into the zeolite should be such as to give concentrations effective in providing the desirable properties of increased aromatics yield when the inventive catalyst system is employed in the conversion of oxygenated hydrocarbons.

The impregnated zeolite, which may or may not have been acid-leached and may or may not have been combined with a binder, can be dried. The drying step is generally performed in the presence of air at a temperature in the range of from about 20° C. to about 125° C. and over a time period of from about 0.1 hour to about 4 hours.

It can be desirable to subject the impregnated zeolite to a thermal treatment in hot air, i.e., calcination, or steam, or both. Preferably, the impregnated zeolite is subjected to a steam treatment whereby it is exposed by any suitable means or method(s) known in the art to an atmosphere of steam under process conditions that suitably provide a steam-treated impregnated zeolite. The zeolite is exposed to a predominantly gaseous atmosphere, preferably an entirely gaseous atmosphere, comprising steam and also an inert gas, such as helium. The steam atmosphere preferably has a concentration of steam, less any inert gas, exceeding about 90 molar percent and, most preferably, the concentration of steam, less any inert gas, exceeds about 95 molar percent. Preferably, the steam is superheated and not saturated.

The steam treatment can be conducted at any pressure and temperature conditions that suitably provide the second solid material. Generally, the steam treatment can be conducted at a pressure in the range of from about 0 atm to about 50 atm, preferably in the range of from about 0.1 atm to about 30 atm, and most preferably from 0.5 atm to 10 atm. The steam treatment temperature is generally in the range of from about 100° C. to about 1000° C., preferably in the range of from about 450° C. to about 975° C., and more preferably, in the range of from 475° C. to 950° C.

Generally, the time period for exposing the metal-promoted zeolite to the atmosphere of steam at appropriate temperature conditions can be in the range of from about 0.1 hour to about 30 hours, preferably in the range of from about 0.25 hour to about 25 hours and, most preferably, in the range of 0.5 hour to 20 hours.

The impregnated zeolite can also be subjected to calcination under suitable calcining conditions. Suitable calcining conditions include a temperature in the range of from about 200° C. to about 1,000° C., preferably in the range of from about 300° C. to about 750° C., and most preferably in the range of from 350° C. to 650° C. and a pressure in the range of from about 0 atm to about 50 atm, preferably in the range of from about 0.1 atm to about 30 atm, and most preferably in the range of from 0.5 atm to 10 atm for a time period in the range of from about 0.1 hour to about 30 hours, preferably in the range of from about 2 hours to about 20 hours, and most preferably in the range of from 3 hours to 15 hours. Preferably, the impregnated zeolite is calcined in air.

The weight percent of the compound comprising zinc and a metal selected from the group consisting of Group IIIA and Group VIB present in the second solid material is generally in the range upwardly to about 10 weight percent based on the total weight of the second solid material. The preferred concentration of the compound in the second solid material is in the range of from about 0.05 to about 9 weight percent and, most preferably, from 0.1 to 8 weight percent based on the total weight of the second solid material.

The weight percent of the compound comprising zinc and a metal selected from the group consisting of Group IIIA and Group VIB present in the second solid material can be measured using X-ray fluorescence analysis, as described in "Spectrometry: Principles and Practices in X-Ray Spectrometric Analysis" by Eugene Burton, 2nd edition.

According to the second embodiment of the present invention, the first solid material and the second solid material can be combined by any means known to those skilled in the art such as stirring or blending, preferably in a dry inert gas atmosphere, to produce the inventive catalyst system. The calcination of the first solid material and/or the calcination of the second solid material can be performed either before or after the combination of the first and second solid materials. The weight ratio of the first solid material to the second solid material in the catalyst system is in the range of from about 1:40 to about 10:1, preferably from about 1:20. to about 4:1, and most preferably from 1:10 to 3:1.

According to the third embodiment of the present invention, the catalyst system can be prepared by placing the first solid material into a contacting vessel and placing the second solid material into the contacting vessel such that a hydrocarbon feedstock comprising at least one oxygenated hydrocarbon charged to the contacting vessel contacts the first solid material prior to contacting the second solid material.

According to the fourth embodiment of the present invention, the catalyst system can be prepared by placing the first solid material into a first contacting vessel, placing the second solid material into a second contacting vessel, and operating the catalyst system such that a hydrocarbon feedstock comprising at least one oxygenated hydrocarbon charged to the catalyst system contacts the first solid material prior to contacting the second solid material.

According to the fifth embodiment of the present invention, a process for the conversion of a hydrocarbon feedstock comprising at least one oxygenated hydrocarbon to a reaction product comprising at least one aromatic comprises, consists essentially of, or consists of contacting the hydrocarbon feedstock with a catalyst system under conditions sufficient to effect the conversion of at least a portion of the hydrocarbon mixture to an aromatic hydrocarbon. The catalyst system can be the same as that disclosed in the first embodiment of the invention and can be produced by the method of the second, third or fourth embodiment of the invention.

Any suitable hydrocarbon feedstock, which comprises oxygenated hydrocarbons, can be used as the feed to be contacted with the inventive catalyst system under suitable process conditions for obtaining a reaction product comprising aromatics. The aliphatic moieties of the oxygenated hydrocarbons preferably contain in the range of from about 1 to about 10 carbon atoms, and more preferably, contain from about 1 to about 4 carbon atoms. Representative oxygenated hydrocarbons include, but are not limited to, lower straight or branched chain alcohols, their unsaturated counterparts and the nitrogen, halogen and sulfur analogues of such. Examples of suitable compounds include, but are not limited to, methanol; isopropanol; n-propanol; ethanol; fuel alcohols; methyl mercaptan; methyl sulfide; methyl amine; dimethyl ether; ethyl mercaptan; ethyl chloride; diethyl ether; methylethyl ether; formaldehyde; dimethyl ketone; acetic acid; n-alkyl amines; n-alkyl halides and n-alkyl sulfides wherein the n-alkyl groups contain 3 to 10 carbon atoms; and combinations or mixtures of any two or more thereof. The presently preferred oxygenated hydrocarbon is methanol.

The hydrocarbon feedstock can be contacted, by any suitable manner, with the inventive catalyst system described herein contained within a conversion reaction zone(s) which will provide the desired conversion to aromatics. The contacting step can be operated as a batch process step or, preferably, as a continuous process step. In the latter operation, a solid catalyst bed or a moving catalyst bed or a fluidized catalyst bed can be employed. Any of these operational modes have advantages and disadvantages, and those skilled in the art can select the one most suitable for a particular feed and catalyst.

The contacting step is preferably carried out within a conversion reaction zone(s), wherein is contained the inventive catalyst system, and under reaction conditions that suitably promote the formation of aromatics, preferably xylenes, from at least a portion of the oxygenated hydrocarbons of the hydrocarbon feedstock. The reaction temperature of the contacting step is generally in the range of from about 200° C. to about 800° C., preferably from about 250° C. to about 750° C. and, most preferably, from 300° C. to 700° C. The contacting pressure can generally range from about 0 psig to about 500 psig, preferably, from about atmospheric pressure to about 450 psig and, most preferably, from atmospheric pressure to 400 psig.

The flow rate at which the hydrocarbon feedstock is charged to the conversion reaction zone(s) is such as to provide a weight hourly space velocity ("WHSV") in the range of from about 0.01 hour$^{-1}$ upwardly to about 1000 hours$^{-1}$. The term "weight hourly space velocity", as used herein, shall mean the numerical ratio of the rate at which a hydrocarbon feedstock is charged to the conversion reaction zone(s) in pounds per hour divided by the pounds of catalyst contained in the conversion reaction zone(s) to which the hydrocarbon feedstock is charged. The preferred WHSV of the feed to the conversion reaction zone(s) or contacting zone(s) can be in the range of from about 0.25 hour$^{-1}$ to about 250 hours$^{-1}$ and, most preferably, from 0.5 hour$^{-1}$ to 100 hours$^{-1}$.

The process is generally carried out in the presence of one or more inert diluents which can be present in an amount in the range of from about 1 to about 99 molar percent, based on the total number of moles of all feed and diluent components fed to the reaction zone. Suitable diluents include, but are not limited to, helium, argon, nitrogen, carbon monoxide, carbon dioxide, hydrogen, water, paraffins, hydrocarbons (such as methane and the like), aromatic compounds, and mixtures of any two or more thereof. The presently preferred diluent is water.

The following examples are provided to further illustrate this invention and are not to be considered as unduly limiting the scope of this invention.

EXAMPLE I

This example illustrates the preparation of catalysts which were subsequently tested as catalysts in the conversion of methanol to aromatics (BTX).

Catalyst A

A 10.0 gram quantity of a commercially available SAPO-34 (provided by UOP, LLC, Des Plaines, Ill. under product designation SAPO-34) was mixed with a 10.0 gram quantity of a colloidal silica solution (provided by Dupont under product designation Ludox®AS-40). The formed mixture was then extruded into ⅟₁₆" diameter pellets and dried at room temperature followed by calcining at a temperature of 538° C. for 6 hours.

Catalyst B

A 28.0 gram quantity of a commercially available HZSM-5 (provided by Chemische Fabrik Uetikon, Corp. of Switzerland under product designation Zeocat® PZ 2/50H) was mixed with 2.8 grams of zinc hexaborate and 32.4 grams of a colloidal silica solution (provided by DuPont, Delaware under product designation Ludox® AS-40). The formed mixture was then extruded into ⅟₁₆" diameter pellets and dried at room temperature. The above steps were repeated and the mixtures were combined followed by steaming at 650° C. for 4 hours.

EXAMPLE II

This example illustrates the use of the catalysts described in Example I in the conversion of methanol to aromatics, in particular xylenes.

In Run 1, a 1.78 gram quantity of Catalyst A described in Example I was placed into a stainless steel tube reactor (length: about 18 inches; inner diameter: about 0.5 inch). The reactor tube was heated to about 450° C. The reactor pressure was about 0 psig. A methanol/water feed, comprising 20 mole % methanol and 80 mole % water, was introduced to the reactor tube at a flow rate of 25 mL/hour to yield a methanol WHSV of about 4.0 hour$^{-1}$. The product was analyzed by means of a gas chromatograph. Test data results obtained after about 7.2 hours on stream are summarized in the Table.

In Run 2, a 2.77 gram quantity of Catalyst B described in Example I was placed into a stainless steel tube reactor (length: about 18 inches; inner diameter: about 0.5 inch). The reactor tube was heated to about 450° C. The reactor pressure was about 0 psig. A methanol/water feed, comprising 20 mole % methanol and 80 mole % water, was introduced to the reactor tube at a flow rate of 25 mL/hour to yield a methanol WHSV of about 2.6 hour$^{-1}$. The product was analyzed by means of a gas chromatograph. Test data results obtained after about 6.7 hours on stream are summarized in the Table.

In Run 3, a 2.89 gram quantity of Catalyst B described in Example I was placed into a stainless steel tube reactor (length: about 18 inches; inner diameter: about 0.5 inch) and a 1.91 gram quantity of Catalyst A was placed on top of Catalyst B in the same reactor tube. The reactor tube was heated to about 450° C. The reactor pressure was about 0 psig. A methanol/water feed, comprising 20 mole % methanol and 80 mole % water, was introduced to the reactor tube, downwardly, at a flow rate of 25 mL/hour to yield a methanol WHSV of about 1.5 hour$^{-1}$. The product was analyzed by means of a gas chromatograph. Test data results obtained after about 7.5 hours on stream are summarized in the Table.

In Run 4, a 2.0 gram quantity of Catalyst A described in Example I was mixed with a 3.0 gram quantity of Catalyst B described in Example I and 150 nL of water. The mixture was then filtered, dried at room temperature, and calcined at 538° C. for 1 hour. The resulting mixture, which had a mass of 5.0 grams, was placed into a stainless steel tube reactor (length: about 18 inches; inner diameter: about 0.5 inch). The reactor tube was heated to about 450° C. The reactor pressure was about 0 psig. A methanol/water feed, comprising 20 mole % methanol and 80 mole % water, was introduced to the reactor tube, downwardly, at a flow rate of 25 mL/hour to yield a methanol WHSV of about 1.4 hour$^{-1}$. The product was analyzed by means of a gas chromatograph. Test data results obtained after about 7.0 hours on stream are summarized in the Table.

TABLE

| Run | Catalyst | Methanol Conversion wt. % | ΣBTX Selectivity[1] wt. % | ΣXylenes Selectivity[2] wt. % |
|---|---|---|---|---|
| 1 | A (control) | 100.0 | 0.0 | 0.0 |
| 2 | B (control) | 100.0 | 1.1 | 0.9 |
| 3 | A & B (invention) (sequential) | 100.0 | 31.3 | 25.3 |
| 4 | A & B (invention) (physically mixed) | 100.0 | 10.3 | 6.9 |

[1]ΣBTX selectivity is defined as the weight % of the ΣBTX in the product divided by the weight % methanol conversion, multiplied by 100.
[2]ΣXylenes selectivity is defined as the weight % of the ΣXylenes in the product divided by the weight % methanol conversion, multiplied by 100.

The test data presented in the Table show that use of the inventive Catalysts in Runs 3 and 4 result in considerably increased ΣBTX selectivity and ΣXylenes selectivity as compared to the use of control Catalysts A (Run 1) and B (Run 2) used alone.

That which is claimed is:

1. A process for converting at least a portion of a hydrocarbon feedstock comprising at least one oxygenated hydrocarbon to a reaction product comprising at least one aromatic, wherein said process comprises contacting said hydrocarbon feedstock at conversion conditions to convert at least a portion of said feedstock to said reaction product with a catalyst system comprising:
   a contacting vessel defining a reaction zone that contains a first distinct layer of a first solid material and a second distinct layer of a second solid material wherein said first solid material comprises a silicoaluminophosphate and said second solid material comprises a zeolite and a compound containing zinc and a metal selected from the group consisting of Group IIIA metals and Group VIB metals.

2. A process as recited in claim 1 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hour$^{-1}$.

3. A process as recited in claim 1 wherein said at least one oxygenated hydrocarbon comprises methanol.

4. A process for converting at least a portion of a hydrocarbon feedstock comprising at least one oxygenated hydrocarbon to a reaction product comprising at least one aromatic, wherein said process comprises contacting said hydrocarbon feedstock at conversion conditions to convert at least a portion of said feedstock to said reaction product with a catalyst system comprising:
   a first solid material comprising a silicoaluminophosphate comprising SAPO-34 having been calcined at a temperature in the range of from about 200° C. to about 1000° C. for a time period in the range of from about 0.1 hour to about 30 hours;
   a second solid material comprising zinc, boron and a zeolite comprising ZSM-5, said second solid material prepared by a method comprising:
   mixing said zeolite with a compound comprising zinc hexaborate to form an impregnated zeolite; steaming said impregnated zeolite at a temperature in the range of from about 100° C. to about 1000° C. for a time period in the range of from about 0.1 hour to about 30 hours to thereby form said second solid material; and
   wherein said compound is present in said second solid material in an amount in the range of from about 0.05 to about 10 weight % based on the total weight of said second solid material.

5. A process as recited in claim 4 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hour$^{-1}$.

6. A process as recited in claim 4 wherein said at least one oxygenated hydrocarbon comprises methanol.

7. A process for converting at least a portion of a hydrocarbon feedstock comprising at least one oxygenated hydrocarbon to a reaction product comprising at least one aromatic, wherein said process comprises contacting said hydrocarbon feedstock at conversion conditions to convert at least a portion of said feedstock to said reaction product with a catalyst system prepared by the method comprising blending:
   a first solid material comprising a silicoaluminophosphate; and
   a second solid material comprising a zeolite and a compound selected from the group consisting of zinc hexaborate, zinc molybdate, zinc chromate, zinc tungstate, and zinc aluminate.

8. A process as recited in claim 7 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hour$^{-1}$.

9. A process as recited in claim 7 wherein said at least one oxygenated hydrocarbon comprises methanol.

10. A process for converting at least a portion of a hydrocarbon feedstock comprising at least one oxygenated hydrocarbon to a reaction product comprising at least one aromatic, wherein said process comprises contacting said hydrocarbon feedstock at conversion conditions to convert at least a portion of said feedstock to said reaction product with a catalyst system prepared by the method comprising:
   placing a first solid material comprising a silicoaluminophosphate into a contacting vessel and placing into said contacting vessel a second solid material comprising a zeolite having incorporated therein a compound selected from the group consisting of zinc hexaborate, zinc molybdate, zinc chromate, zinc tungstate, and zinc aluminate wherein such thus incorporated zeolite has been subjected to a thermal treatment.

11. A process as recited in claim 10 wherein said conversion conditions include a temperature in the range of from about 200° C. to about 800° C., a pressure in the range of from about 0 psig to about 500 psig, and a weight hourly space velocity in the range of from about 0.01 hour$^{-1}$ to about 1000 hour$^{-1}$.

12. A process as recited in claim 10 wherein said at least one oxygenated hydrocarbon comprises methanol.

13. A process for converting at least a portion of a hydrocarbon feedstock comprising at least one oxygenated hydrocarbon to a reaction product comprising at least one aromatic, wherein said process comprises contacting said hydrocarbon feedstock at conversion conditions to convert at least a portion of said feedstock to said reaction product with a catalyst system prepared by the method comprising:

placing a first solid material comprising a silicoaluminophosphate into a first contacting vessel;

placing a second solid material into a second contacting vessel, said second solid material comprises a zeolite having incorporated therein a compound selected from the group consisting of zinc hexaborate, zinc molybdate, zinc chromate, zinc tungstate, and zinc aluminate wherein such thus incorporated zeolite has been subjected to a thermal treatment; and operatively relating said first contacting vessel to said second contacting vessel such that hydrocarbon feedstock comprising at least one oxygenated hydrocarbon charged to said catalyst system contacts said first solid material prior to contacting said second solid material.

14. A process as recited in claim 13 wherein said conversion conditions include a temperature in the range of from about 200° C. to about 800° C., a pressure in the range of from about 0 psig to about 500 psig, and a weight hourly space velocity in the range of from about 0.01 $hour^{-1}$ to about 1000 $hour^{-1}$.

15. A process as recited in claim 13 wherein said at least one oxygenated hydrocarbon comprises methanol.

\* \* \* \* \*